United States Patent [19]

Grindey et al.

[11] Patent Number: 5,464,826
[45] Date of Patent: Nov. 7, 1995

[54] METHOD OF TREATING TUMORS IN MAMMALS WITH 2',2'-DIFLUORONUCLEOSIDES

[75] Inventors: Gerald B. Grindey; Larry W. Hertel, both of Indianapolis, Ind.

[73] Assignee: Eli Lilly and Company, Indianapolis, Ind.

[21] Appl. No.: 280,687

[22] Filed: Jul. 26, 1994

Related U.S. Application Data

[62] Division of Ser. No. 99,268, Jul. 29, 1993, abandoned, which is a continuation of Ser. No. 746,441, Aug. 16, 1991, abandoned, which is a division of Ser. No. 163,571, Mar. 3, 1988, Pat. No. 5,061,793, which is a continuation of Ser. No. 786,419, Oct. 10, 1985, abandoned, which is a continuation-in-part of Ser. No. 677,783, Dec. 4, 1984, abandoned.

[51] Int. Cl.⁶ .................... A61K 31/70; C07H 19/073
[52] U.S. Cl. ............................... 514/50; 514/49
[58] Field of Search ............................ 514/49, 50

[56]   References Cited

U.S. PATENT DOCUMENTS

| | | | |
|---|---|---|---|
| 3,705,147 | 12/1972 | Robins | 536/28.1 |
| 3,870,700 | 3/1975 | Kotick et al. | 536/28.53 |
| 4,058,602 | 11/1977 | Beisler et al. | 514/43 |
| 4,145,531 | 3/1979 | Eckstein et al. | 536/27.11 |
| 4,211,773 | 7/1980 | Lopez et al. | 514/49 |
| 4,526,988 | 7/1985 | Hertel | 536/27.6 |
| 4,692,434 | 9/1987 | Hertel | 536/18.4 |
| 4,808,614 | 2/1989 | Hertel | 536/27.4 |
| 4,914,028 | 4/1990 | Hertel et al. | 435/88 |
| 4,983,724 | 1/1991 | Hertel et al. | 536/4.1 |
| 5,015,743 | 5/1991 | Hertel | 549/313 |
| 5,061,793 | 10/1991 | Grindey et al. | 536/27.14 |

FOREIGN PATENT DOCUMENTS

| | | |
|---|---|---|
| 122707 | 10/1984 | European Pat. Off. . |
| 0345751 | 12/1989 | European Pat. Off. . |
| 147774 | 4/1981 | Germany . |
| 5136467 | 3/1976 | Japan . |

OTHER PUBLICATIONS

Brox, et al., Growth Inhibition of 2'-Deoxy-2'-Fluorocytidine, *Chem. Abstr.*, 82:25625 (1975).
Adamson, et al., 2-Deoxy-2,2,difluoro-D-Arabinohexose, *Chem. Abstr.*, 75:98773a (1971).
Sweeney, et al., *Cancer Research*, 38, 2886–91 (1978).
Derwent Abstract 51749 D/29, 1976.
Derwent Abstract 35195 X/19, 1976.
Chou, et al., *Cancer Res.*, 42, 3957–63 (1982).
Burchenal, et al., *Cancer Res.*, 42, 2598–600 (1982).
Martin, et al., *Jour. Pharm. Sci.*, 76 (No. 2) 180–84 (1987).
*Remington's Pharmaceutical Sciences*, 16th ed., Osol ed., Mack Publishing Co., 424 (1980).
Miller, et al., *Jour. of Med. Chem.*, 20 (No. 3) 409–13 (1977).
Frei, *Cancer Research*, 45, 6523–37 (1985).
Physicians' Desk References (1984).
Goodman and Gilman's, The Pharmacological Basis of Therapeutics, 6th Ed. (1980).
Yamauchi, et al., *J. Chem. Soc.*, Perkin Trans. I, 12, pp. 2787–2792, (1980).
Mattern et al. Cancer and Metastasis Reviews 7:263–284, 1988.

*Primary Examiner*—Douglas W. Robinson
*Assistant Examiner*—Gary L. Kunz
*Attorney, Agent, or Firm*—Robert A. Conrad

[57]   ABSTRACT

A method of treating susceptible neoplasms in mammals comprising administering to a mammal in need of such treatment a pharmaceutically effective amount of a compound of the formula

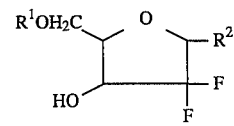

wherein:
  $R^1$ is hydrogen;
  $R^2$ is a base defined by one of the formulae

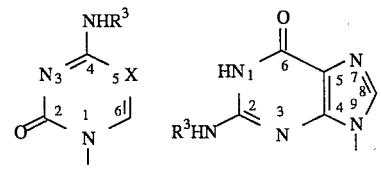

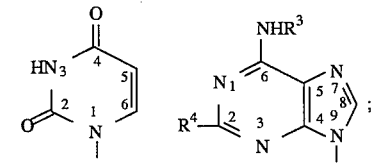

X is $C-R^4$;
$R^3$ is hydrogen;
$R^4$ is hydrogen, $C_1$–$C_4$ alkyl, bromo, fluoro, chloro or iodo;
and the pharmaceutically-acceptable salts thereof.

7 Claims, No Drawings

METHOD OF TREATING TUMORS IN MAMMALS WITH 2',2'-DIFLUORONUCLEOSIDES

CROSS REFERENCE TO RELATED APPLICATION

This application is a division of application Ser. No. 08/099,268, filed Jul. 29, 1993, now abandoned, which is a continuation of application Ser. No 07/746,441, filed Aug. 16, 1991, now abandoned, which is a division of application Ser. No. 07/163,571, filed Mar. 3, 1988, now U.S. Pat. No. 5,061,793, which is a continuation of application Ser. No. 06/786,419, filed Oct. 10. 1985, now abandoned, which is a continuation-in-part of application Ser. No. 06/677,783, filed Dec. 4, 1984, now abandoned.

BACKGROUND OF THE INVENTION

While the treatment of cancer was once considered impossible, great strides have been made during the past ten years in controlling the ravages of this often fatal disease. Several drugs which contribute to the increasing rate of survival are now routinely used clinically. The most commonly employed antitumor agents include methotrexate, doxorubicin and the vinca alkaloids such as vincristine. However, research continues to develop more effective compounds with greater safety for subjects under treatment. This invention provides an additional method of treating tumors.

SUMMARY OF THE INVENTION

The present invention provides a method of treating susceptible neoplasms in mammals comprising administering to a mammal in need of such treatment a pharmaceutically effective amount of a compound of the formula

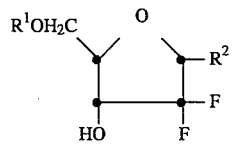           I wherein:
$R^1$ is hydrogen or

$R^2$ is a base defined by one of the formulae

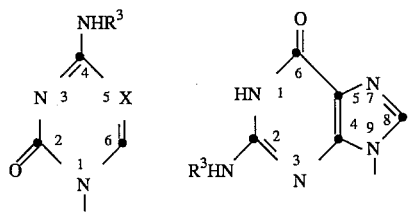

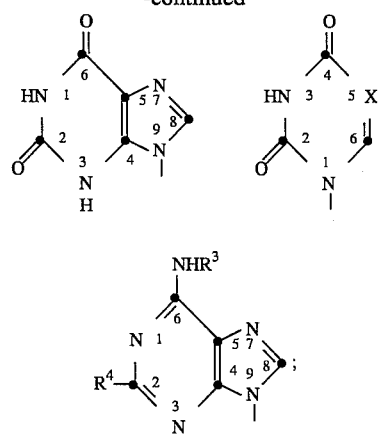

$X$ is N or $C-R^4$;
$R^3$ is hydrogen, $C_1-C_4$ alkyl or

$R^4$ is hydrogen, $C_1-C_4$ alkyl, amino, bromo, fluoro, chloro or iodo;
each $R^5$ independently is hydrogen or $C_1-C_4$ alkyl; and
the pharmaceutically-acceptable salts thereof.

The present invention also provides a novel compound of the formula

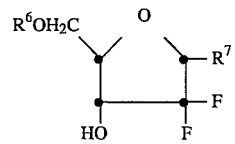           II wherein:
$R^6$ is hydrogen or $C_1-C_4$ alkyl;
$R^7$ is a base of one of the formulae

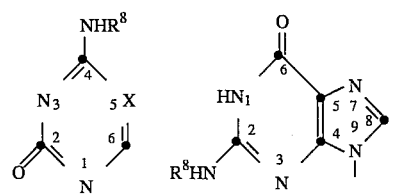

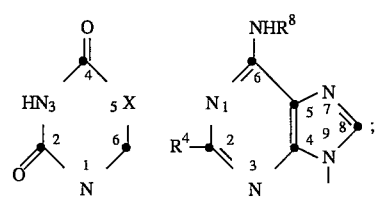

$X$ is N or $C-R^4$;
$R^8$ is hydrogen or $C_1-C_4$ alkyl;
$R^4$ is hydrogen, $C_1-C_4$ alkyl, amino, bromo, fluoro, chloro and iodo; and
the pharmaceutically-acceptable salts thereof; with the proviso that $R^6$ and $R^8$ may both be hydrogen only when X is N.

The present invention further provides a compound of the formula

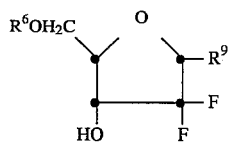

III wherein:
$R^6$ is hydrogen or $C_1$–$C_4$ alkyl;

$R^9$ is 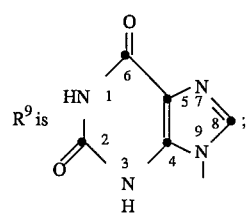;

and
the pharmaceutically-acceptable salts thereof.

The present invention also provides pharmaceutical formulations useful for treating susceptible neoplasms in mammals comprising a compound of formula I with a suitable pharmaceutically acceptable carrier, diluent or excipient therefor.

DETAILED DESCRIPTION OF THE INVENTION

The compounds employed in the present invention are preferably prepared by reacting a D-glyceraldehyde ketonide with a $C_1$–$C_4$ alkyl bromodifluoroacetate to afford an alkyl 3-dioxolanyl-2,2-difluoro-3-hydroxypropionate. The hydroxypropionate is hydrolyzed to a lactone which is protected and reduced to afford a 2-desoxy-2,2-difluororibose or xylose derivative. The hydroxy group of this compound is provided with a leaving group, and the resulting carbohydrate is coupled with an appropriate base. The resulting protected nucleoside is finally deprotected to provide a compound for use in the present method. The overall reaction scheme is illustrated as follows:

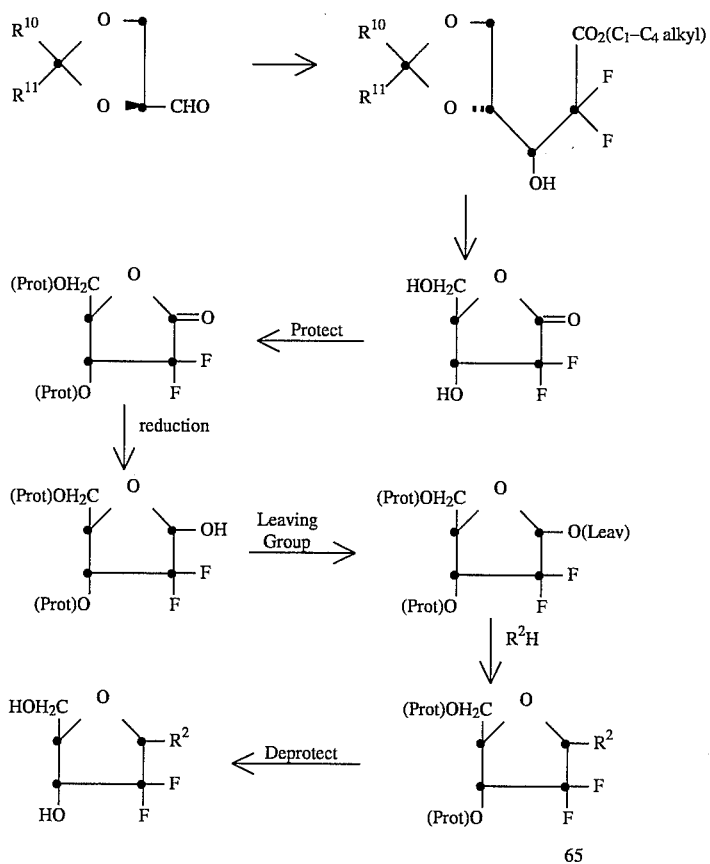

wherein $R^{10}$ and $R^{11}$ independently are $C_1$–$C_3$ alkyl,

"Prot" is a hydroxy protecting group and "Leav" is a leaving group.

It generally is desirable to convert free hydroxy groups to protected hydroxy groups during coupling of the 2-desoxy-2,2-difluorocarbohydrate to a base. The protecting groups are those commonly used in synthetic organic chemistry. Chemists are accustomed to choosing groups which can be placed efficiently on hydroxy groups, and which can be removed easily when the reaction is complete. Suitable groups may be those described in standard textbooks, such as Chapter 3 of *Protective Groups in Organic Chemistry*, McOmie, Ed., Plenum Press, New York (1973); and Chapter 2 of *Protective Groups in Organic Synthesis*, Greene, John Wiley & Sons, New York (1981).

Hydroxy-protecting groups commonly employed include formyl,

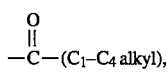

2-chloroacetyl, benzyl, diphenylmethyl, triphenylmethyl, 4-nitrobenzyl, phenoxycarbonyl, $C_1$–$C_4$ alkyl such as t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, and benzyloxycarbonyl. Silyl hydroxy-protecting groups are particularly convenient because most of them are cleaved easily by contact with water or an alcohol. Such groups may include especially trimethylsilyl, as well as isopropyldimethylsilyl, methyldiisopropylsilyl, or triisopropylsilyl. The t-butyldimethylsilyl group is a special case and is preferred as the protecting group in this synthesis; it is more difficult to cleave, requiring a reagent such as a hydrohalic acid to remove it from the hydroxy groups.

Ribose or xylose has a hydroxy group at the 1-position of its ring. In order to react the carbohydrate with the base, to form the compounds employed in this invention, a leaving group must be placed at the 1-position. The leaving groups are those typically used in organic synthesis. The preferred leaving groups are sulfonates, of which the most preferred is methanesulfonate. Other typical leaving groups such as toluenesulfonate, ethanesulfonate, isopropanesulfonate, 4-methoxybenzenesulfonate, 4-nitrobenzenesulfonate, 2-chlorobenzenesulfonate, chloro and bromo also may be used.

The carbohydrates employed in the synthesis of the compounds employed in the present invention are prepared by reacting a D-glyceraldehyde ketonide of the formula

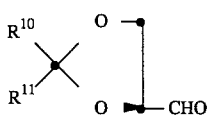

wherein $R^{10}$ and $R^{11}$ are as defined above with a $C_1$–$C_4$ alkyl bromodifluoroacetate, preferably the ethyl ester.

The preferred glyceraldehyde ketonide is the acetonide in which $R^{10}$ and $R^{11}$ are both methyl (see Fischer and Baer, *Helv. Chim. Acta.* 17, 622 (1934)). Ethyl bromodifluoroacetate was prepared first by Morel and Dawans, *Tet.* 33, 1445 (1977). The reaction of the ketonide and the haloacetate is carried out in the presence of an activated metal such as magnesium or preferably zinc. Activation is obtained most easily by applying ultrasonic energy to the reaction mixture. Activation by that means compensates for the presence of a small amount of water in the reaction mixture, avoiding the necessity to maintain anhydrous conditions, and also avoids the necessity to prepare and carefully store activated metals. However, if desired, the metal may be activated by the customary methods known in the art. Approximately an equimolar amount of metal is the most advantageous amount.

The reaction has been performed in ethers such as tetrahydrofuran and diethyl ether, at moderate temperatures. However, other organic solvents which are inert to the reaction conditions may be used, including halogenated alkanes such as chloroform, dichloromethane, or trichloroethane, and aromatic solvents including benzene, toluene and the xylenes. Temperatures in the range of from about ambient temperature to about 150° C. may be used; temperatures from about ambient temperature to about 80° C. are preferred, however. Economically-acceptable yields have been obtained in reaction times ranging from a few minutes to a few hours. One should note that the reaction is exothermic, and the mixture may need to be cooled, depending on the scale of the reaction and the rate at which the reactants are added.

The product of the first reaction is an alkyl 3-dioxolanyl-2,2-difluoro-3-hydroxypropionate of the formula

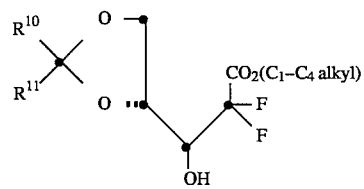

in which $R^{10}$ and $R^{11}$ are as described above.

The ratio of the 3-R-hydroxy intermediate to its 3-S-hydroxy enantiomer is usually about 3:1. The 3-R-hydroxy enantiomer has the proper stereochemistry to produce the ribose derivative in its natural configuration, and so it is the desired enantiomeric product of the first step. The 3-R-hydroxy enantiomer can generally be separated cleanly from the 3-S-enantiomer by chromatography on silica gel, eluting with chloroform containing 0.5% methanol.

The hydroxypropionate, in either form, is hydrolyzed using very mild conditions to form the lactone of the formula

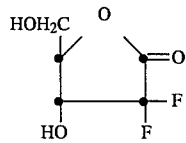

Proper control of the hydrolysis step will cleave the ketonide function and the ester group, providing the lactone in a single step. The hydrolysis reagent preferably is a mildly acidic ion exchange resin, of which Dowex 50W-X12 (Dow Chemical Company) is most highly preferred. Other mild hydrolytic reagents may be employed although larger amounts of by-products may be obtained. For example, aqueous acetic acid, or other relatively strong acids such as propionic acid, formic acid, chloroacetic acid, or oxalic acid may be used for the hydrolysis.

The hydroxy groups of the lactone should be protected before its keto oxygen is reduced. The usual reaction conditions are used, depending on the protecting groups chosen. For example, the t-butyldimethylsilyl group is most conveniently provided in the form of its trifluoromethanesulfonate, and the protection reaction is carried out in the presence of a base such as lutidine, pyridine and the like. Acyl protecting groups such as acetyl, benzoyl and the like are added by reacting the lactone with an acylating agent such as an acyl chloride, bromide, cyanide or azide, or with an appropriate anhydride. The reactions are conveniently carried out in a basic solvent such as pyridine, quinoline or isoquinoline, or in a tertiary amine solvent such as triethylamine, tributylamine, or methylpiperidine. The reaction also may be carried out in an inert solvent, to which an acid scavenger, such as a tertiary amine, has been added. Acylation catalysts such as 4-dimethylaminopyridine or 4-pyrrolidinopyridine may be used in the reaction, if desired. The acylation reactions which provide protecting groups on the hydroxy groups are carried out at moderate temperatures in the range of from −25° C. to 100° C. Such acylations also may be performed by acid-catalyzed reactions of the appropriate carboxylic acids, in inert organic solvents or neat. Acid catalysts such as sulfuric acid, polyphosphoric acid, or methanesulfonic acid may be used.

Acyl protecting groups may also be provided by forming an active ester of the appropriate acid, for example esters formed by reaction with reagents such as dicyclohexylcarbodiimide, acylimidazoles, nitrophenols, pentachlorophenol, N-hydroxysuccinimide and 1-hydroxybenzotriazole.

Protected groups of the ether type are produced by reacting the lactone with, for example, an appropriate diazo compound, such as diazomethane, phenyldiazomethane or a silyldiazomethane. Such reactions commonly are carried out in solvents including esters such as ethyl acetate, halogenated solvents including dichloromethane and chloroform, and ethers including diethyl ether and tetrahydrofuran. The process is usually carried out at low temperatures from about −50° C. to about 0° C. Such ether-forming reactions may also be carried out with the assistance of reagents such as trimethyloxosulfonium hydroxide, trimethylsulfonium hydroxide and trimethylselenonium hydroxide, in solvents such as dimethylsulfoxide, dimethylformamide, hexamethylphosphoramide, acetone, or acetonitrile.

The silyl protecting groups discussed above are placed on the hydroxy groups by the conventional methods, such as by reaction with the appropriate silylcarboxamide or bis(substituted-silyl)carboxamide, or an appropriately substituted silazane. Suitably substituted silyl methanesulfonates, toluenesulfonates and the like are useful also. An equivalent amount of a base is usually necessary in the reaction mixture, unless a basic solvent is used in the reaction.

When the hydroxy groups have been protected, the keto oxygen of the lactone is reduced to the alcohol, forming the protected 2-desoxy-2,2-difluororibose or xylose. The most preferred reducing agent is diisobutyl aluminum hydride, used at a low temperature in the range of about −100° C. to −20° C. The reduction must be performed very carefully to avoid conditions so vigorous that the ring is opened at the oxygen atom. Other metal hydrides, such as the widely used lithium aluminum hydride, can also be used for the reduction, but it is necessary to keep the temperature quite low and to assure that the hydride is destroyed before the temperature is allowed to rise above about −20° C. Accordingly, a solvent with a very low freezing point, such as toluene, must be used in the reduction step. Other solvents, of course, can be used, including lower alkanols, especially ethanol, or ethers such as diethyl ether.

To obtain efficient reaction with the base, an appropriate leaving group must be placed at the 1-position of the carbohydrate. The preferred leaving group is methanesulfonyl, and the compound with this leaving group is readily provided by reaction with methanesulfonyl chloride in the presence of an equivalent amount of a suitable acid scavenger such as triethylamine and the like. Other sulfonyl leaving groups are provided in the same way by reaction with the appropriate sulfonyl halide.

When a chloro or bromo leaving group is to be used, it is frequently advantageous first to make the 1-acetate derivative, as by reaction with acetic anhydride, or another source of acetyl groups, in the presence of an equivalent amount or more of an acid scavenger. The acetate group then is displaced, at a low temperature such as about −50° C. to about 0° C., with gaseous hydrogen bromide or hydrogen chloride. Because the gaseous hydrogen halide may tend to remove the protecting groups, especially silyl protecting groups, operating this step at low temperatures and adding the hydrogen halide slowly in small increments is necessary.

The compounds employed in the present invention having a base portion which is composed of a purine substrate are preferably synthesized by reacting the 1-hydroxy analog of the carbohydrate having protecting groups at the 3- and 5-position with the base in the presence of diethyl azodicarboxylate and triphenylphosphine. Standard modifications are then made to the purine substrate if desired.

The bases used to form the compounds employed in the present invention are known to those skilled in the art, and no discussion of their synthesis is necessary. The primary amino groups present on some of the bases, however, should be protected before the base is coupled with the carbohydrate. The usual amino-protecting groups are employed, including silyl groups such as have been discussed, as well as such typical groups as t-butoxycarbonyl, benzyloxycarbonyl, 4-methoxybenzyloxycarbonyl, 4-nitrobenzyloxycarbonyl, formyl, or acetyl.

Converting the keto oxygen atoms on the bases to the enol form, in order to make the base more highly aromatic and allowing a more ready attack of the base by the carbohydrate is advisable. Enolization is provided most conveniently by producing the silyl protecting groups. The usual silyl protecting groups, as discussed above, may be used for this purpose.

The reaction between the protected carbohydrate and the base preferably is performed neat at a temperature in the range of from about 50° C. to about 200° C. Use of relatively high-boiling solvents for the reaction, such as dimethylformamide, dimethylacetamide, or hexamethylphosphoramide, however, is possible. If the coupling reaction is carried out at elevated pressures to avoid distillation of a low-boiling solvent, any convenient inert reaction solvent can be used.

The coupling reaction may be done at low temperatures if a reaction initiator, such as a trifluoromethanesulfonyloxysilane, is used. The usual inert reaction solvents, as discussed above, may be used at temperatures in the range of from about ambient temperature to about 100° C.

The final step of the reaction sequence is the removal of the protecting groups. Most silyl protecting groups are cleaved easily by contact with water or an alcohol. The t-butyldimethylsilyl protecting group requires acid conditions, such as contact with gaseous hydrogen halide, for its removal.

Acyl protecting groups are removed by simple hydrolysis with strong or moderately strong bases, such as alkali metal hydroxides, at temperatures from about ambient temperature to about 100° C. At least one equivalent amount of base is needed for each protecting group. Such hydrolyses conveniently are carried out in hydroxylic solvents, especially aqueous alkanols. The reactions also may be carried out, however, in any convenient solvent, such as polyols including ethylene glycol, ethers such as tetrahydrofuran, ketones such as acetone and methyl ethyl ketone and other polar solvents such as dimethylsulfoxide. The cleavage of acyl protecting groups may also be performed with other bases, including, for example, sodium methoxide, potassium t-butoxide, hydrazine, hydroxylamine, ammonia, alkali metal amides and secondary amines such as diethylamine. The acyl protecting groups also can be removed with acid catalysts, such as methanesulfonic acid, hydrochloric acid, hydrobromic acid, sulfuric acid, or with acidic ion exchange resins. Carrying out such hydrolyses at a relatively high temperature, such as the reflux temperature of the mixture is preferred, but temperatures as low as ambient may be used when particularly strong acids are used.

The removal of protecting groups which are ethers is carried out by known methods, for example, with ethanethiol and aluminum chloride.

Compounds of the invention possessing hydroxy or amino acyl or alkyl groups can, of course, be either selectively deprotected, or such groups may be removed and selectively replaced by standard conditions.

None of the reaction steps require unusual excesses of the reactants. As usual in organic syntheses, use of a moderate excess, in the range of 1.05× to 2×, is advisable.

The compounds employed in this invention are capable of forming pharmaceutically-acceptable addition salts. Such salts are to be construed as included within the scope of this invention and may include hydrobromide, hydrochloride, mono-, di- or triphosphate esters and sodium salts of such phosphates, sulfate, the sodium, potassium, lithium or ammonium salts, as well as others well-known to those skilled in the art. "Pharmaceutically-acceptable salts" are those salts useful in the chemotherapy of warm-blooded animals.

The structural drawings defining the compounds employed in the present invention do not indicate their stereochemistry. Compounds of all configurations are believed to be useful, and the stereochemistry of the compound is not to be construed as a limitation. The preferred compounds possess the configuration of naturally occurring ribose, e.g.,

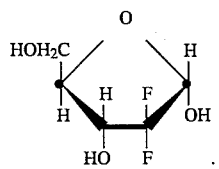

The configuration at the juncture between the ribose and the base is preferably as follows:

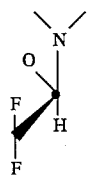

One skilled in the art would be aware of the bases which are used in the synthesis of the nucleosides employed in the present invention, but the following specific nucleosides are given to further elaborate the type of agents which may be used in this invention.

1-(2,4-dioxo-1H,3H-pyrimidin-1-yl)-2-desoxy-2,2-difluororibose
1-(4-amino-5-chloro-2-oxo-1H-pyrimidin-1-yl)-2-desoxy-2,2-difluororibose
1-(4-amino-5-bromo-2-oxo-1H-pyrimidin-1-yl)-2-desoxy-2,2-difluororibose
1-(4-amino-2-oxo-1H-pyrimidin-1-yl)-2-desoxy-2,2-difluororibose
1-(4-amino-5-iodo-2-oxo-1H-pyrimidin-1-yl)-2-desoxy-2,2-difluororibose
1-(4-amino-5-methyl-2-oxo-1H-pyrimidin-1-yl)-2-desoxy-2,2-difluororibose
1-(2-amino-6-oxo-1H,9H-purin-9-yl)-2-desoxy-2,2-difluororibose
1-(6-amino-9H-purin-9-yl)-2-desoxy-2,2-difluororibose
1-(4-amino-5-fluoro-2-oxo-1H-pyrimidin-1-yl)-2-desoxy-2,2-difluororibose
1-(4-amino-5-chloro-2-oxo-1H-pyrimidin-1-yl)-2-desoxy-2,2-difluoroxylose
1-(4-amino-2-oxo-1H-pyrimidin-1-yl)-2-desoxy-2,2-difluoroxylose
1-(4-amino-5-fluoro-2-oxo-1H-pyrimidin-1-yl)-2-desoxy-2,2-difluoroxylose
1-(4-amino-5-methyl-2-oxo-1H-pyrimidin-1-yl)-2-desoxy-2,2-difluoroxylose
1-(2-amino-6-oxo-1H,9H-purin-9-yl)-2-desoxy-2,2-difluoroxylose
1-(6-amino-9H-purin-9-yl)-2-desoxy-2,2-difluoroxylose
or the pharmaceutically-acceptable salts thereof.

The following Examples illustrate specific compounds suitable for use in the present invention. The Examples are not intended to be limiting in any respect to the scope of the invention and should not be so construed.

EXAMPLE 1

1-(4-Amino-2-oxo-1H-pyrimidin-1-yl)-2-desoxy-2,2-difluororibose

To 47.3 g (0.1 mol) of 3,5-bis(t-butyldimethylsiloxy)-1-methanesulfonyloxy-2-desoxy-2,2-difluororibose in 940 ml of dry 1,2-dichloroethane was added 48.0 g (0.16 mol) of bis-trimethylsilyl N-acetylcytosine followed by 39.23 g (0.177 mol) of trifluoromethanesulfonyloxytrimethylsilane. The reaction mixture was refluxed under a nitrogen atmosphere for about 15 hours, cooled to room temperature, and diluted by the addition of 16 ml of methanol. The resulting mixture was stirred for 30 minutes, concentrated under vacuum to about one-half the original volume and cooled in ice. The precipitated solid was collected by filtration and the filtrate was shaken one time with about 300 ml of 10% sodium bicarbonate and one time with brine. The organic layer was separated and concentrated to dryness in vacuo at 45° C. The residue was dissolved into 1.3 l. of methanol saturated with ammonia and the resulting solution was stirred overnight. The volatiles were removed in vacuo at 45° C. to provide 32 g of residue. The residue was dissolved into 275 ml of methanol and 100 g of Biorad cation exchange resin (AG50WXS) was added to the resulting solution. The suspension was stirred at ambient temperature overnight. The resin was removed by filtration and rinsed one time with 100 ml of methanol. The filtrate was discarded and the resin was suspended in 100 ml of methanol and 50 ml of concentrated ammonium hydroxide. This mixture was stirred vigorously for 15 minutes and the resin was filtered. This procedure was repeated two times with additional fresh methanolic ammonia. The basic methanolic filtrates were combined and evaporated at 45° C. in vacuo to yield a brown foam weighing 13.8 grams. This material was chromatographed with the use of a Waters Prep 500 $C_{18}$ reverse phase column with 100% water to yield 1.26 g of 1-(4-amino-2-oxo-1H-pyrimidin-1-yl)-2-desoxy-2,2-difluororibose.

NMR ($CD_3OD$, 90 mHz, δ) 3.7–4.65 (m, 4H), 4.83 (s, 4H), 5.97 (d, J=8 Hz, 1H), 6.24 (t, J=7 Hz, 1H, 7.88 (d, J=8 Hz, 1H). Mass spec. m/e=263=P

EXAMPLE 2

1-(4-Amino-5-iodo-2-oxo-1H-pyrimidin-1-yl)-2-desoxy-2,2-difluororibose

To 1.99 g (0.0042 mol) of 3,5-bis(t-butyldimethylsiloxy)-1-methanesulfonyloxy-2-desoxy-2,2-difluororibose in 35 ml of dry 1,2-dichloroethane was added 2.08 g (0.0046 mol) of tris-trimethylsilyl-5-iodocytosine followed by 1.11 g (0.005 mol) of trifluoromethanesulfonyloxytrimethylsilane. The reaction mixture was refluxed for about 16 hours under a nitrogen atmosphere and cooled to room temperature. Five milliliters of methanol were added to the reaction mixture and the mixture was stirred for an additional 30 minutes. The mixture was filtered and the precipitated solid was collected by filtration. The filtrate was evaporated to dryness under reduced pressure, and the resulting residue was dissolved in 20 ml of dichloromethane saturated with anhydrous hydrogen bromide. This mixture was stirred for about 3 hours. The volatiles were removed in vacuo at 45° C. The residue was dissolved in 15 ml of water, neutralized to pH 7–8 with 10% sodium bicarbonate, and the resulting solution was washed once with 10 ml of ethyl acetate. The aqueous layer was chromatographed on a Whatman Prep ODS-3 reverse phase column in 2.0 ml portions using water/methanol (9:1, v:v) to afford 30 mg of 1-(4-amino-5-iodo-2-oxo-1H-pyrimidin-1-yl)-2-desoxy-2,2-difluororibose.

NMR ($CD_3OD$, 90 mHz, δ) 3.47–4.66 (m, 4H), 4.78 (s, 4H), 6.14 (t, J=7 Hz, 1H), 8.32 (s, 1H). Mass spec. m/e=389=P

EXAMPLE 3

1-(2,4-Dioxo-1H, 3H-pyrimidin-1-yl)-2-desoxy-2,2-difluororibose

A solution of 190 mg (0.0007 mol) of 1-(4-amino-2-oxo-1H-pyrimidin-1-yl)-2-desoxy-2,2-difluororibose in 16 ml of glacial acetic acid and 4 ml of water was refluxed for approximately 24 hours. The reaction mixture was cooled to ambient temperature and the volatiles were evaporated under vacuum at about 60°–70° C. The residue was stirred with 5.0 ml of toluene and the resulting solution was evaporated several times. The residue was dissolved in 12 ml of methanol, and the resulting mixture was cooled to −15° C. and saturated with anhydrous ammonia. The solution was stirred overnight at ambient temperature. The volatiles were removed in vacuo at 45° C. The residue was suspended in about 5.0 ml of hot water and the insoluble material was removed by filtration. The filtrate was chromatographed on a Whatman 50 cm partisil ODS-3 reverse phase column using water methanol (9:1, v:v) as the eluent to afford 0.05 g of product containing a small trace of unreacted starting material. The unreacted starting material was removed by passing a solution of 0.05 g of the mixture in about 5.0 ml of a solvent solution of methylene chloride/methanol (9:1, v:v) through a Waters Silica Sep-Pak. The eluate was evaporated in vacuo at 45° C. to yield 0.036 g of 1-(2,4-dioxo-1H,3H-pyrimidin-1-yl)-2-desoxy-2,2-difluororibose.

NMR ($CD_3OD$, 90 mHz, δ) 3.54–4.48 (m, 4H), 4.83 (s, 3H), 5.69 (d, J=8 Hz, 1H), 6.10 (dd, J=7 Hz, 9 Hz, 1H), 7.8 (d, J=8 Hz, 1H). Mass spec. m/e=264=P

EXAMPLE 4

1-(4-Amino-5-methyl-2-oxo-1H-pyrimidin-1-yl)-2-desoxy-2,2-difluororibose

A solution of 1.86 g (0.0039 mol) of 3,5-bis(t-butylidimethylsilyloxy)-1-methanesulfonyloxy-2-desoxy-2,2-difluororibose, 1.87 g (0.0055 mol) of bis-trimethylsilyl-5-methylcytosine and 1.34 g (0.006 mol) of trifluoromethanesulfonyloxytrimethylsilane in 37 ml of dry methylene chloride was refluxed overnight. The reaction mixture was cooled to room temperature and 1.0 ml of methanol was added thereto. The precipitated solid was collected by filtration and the filtrate was evaporated in vacuo at 45° C. The residue was dissolved in 20 ml of water and the resulting solution was concentrated to about 10 ml in vacuo at 50° C. at which point a precipitate formed. The precipitated solid was collected by filtration and the filtrate was concentrated in vacuo at 50° C. to afford 2.2 g of residue. The residue was triturated several times with 10 ml portions of warm acetone. The decanted organic layers were combined and evaporated in vacuo at 45° C. to provide 1.67 g of a yellow oil. This material was dissolved into 15 ml of methanol/water (v:v, 1:1) and the resulting solution was stirred overnight with 5.0 g of Biorad AG50WX8. The suspension was saturated with anhydrous ammonia and stirred for 10 minutes. The resin was collected by filtration and suspended in 30 ml of methanol/ammonia (v:v, 2:1). The solution was stirred for 10 minutes. The resin was collected by vacuum filtration, and the basic filtrates were combined and concentrated in vacuo at 50° C. to provide 1.5 g of an orange oil. The oil was dissolved in 10 ml of water and chromatographed 2.0 ml per run on a Whatman partisil ODS-3 50 cm reverse phase prep column using water as the eluent to provide 0.07 g of 1-(4-amino-5-methyl-2-oxo-1H-pyrimidin-1-yl)-2-desoxy-2,2-difluororibose.

NMR ($CD_3OD$, 90 mHz, δ) 1.94 (s, 3H), 3.53–4.62 (m, 4H), 4.75 (s, 4H), 6.17 (t, J=8 Hz, 1H, 7.67 (s, 1H). Mass spec. m/e=277=P

EXAMPLE 5

1-(4-Amino-2-oxo-1H-pyrimidin-1-yl)-2-desoxy-2,2-difluoroxylose

Under a nitrogen atmosphere, to 17.89 g (0.0375 mol) of 3,5-bis(t-butyldimethylsiloxy)-1-methanesulfonyloxy-2-desoxy-2,2-difluoroxylose in 300 ml of dry methylene chloride was added 23.0 g (0.063 mol) of tris-trimethylcytosine followed by 10.84 g (0.0488 mol) of trifluoromethanesulfonyloxytrimethylsilane. The solution was refluxed overnight and cooled to room temperature. Twenty milliliters of methanol were added to the reaction mixture and the resulting solution was stirred vigorously for about one hour. The precipitated solid was collected by filtration. The filtrate was charged with 100 ml of water and the suspension was stirred vigorously for 30 minutes. The organic layer was separated and concentrated in vacuo at 45° C. to give 11.2 g of a brown oil. The oil was dissolved in 95 ml of methanol to which 33 g of Biorad AG50WX8 cation exchange resin had been added and the suspension was stirred overnight at ambient temperature. The resin was collected by filtration and washed with 50 ml of methanol. The resin was stirred vigorously with 100 ml of a solution of methanol/ammonia (v:v, 1:1). The resin was collected by filtration and again stirred in this solution. The resin was collected and the basic filtrates were combined and concentrated in vacuo at 50° C. to give 2.09 g of a yellow residue. This material was suspended in 25 ml of water and stirred vigorously for 15 minutes. The insoluble precipitate was filtered to yield 0.250 g of a compound labeled A. The filtrate was concentrated in vacuo at 50° C. to yield 0.86 g of a compound labeled B. Compound A was dissolved in 20 ml of methanol and stirred for 3 days with Biorad AG5OWX8 at ambient temperature. The resin was collected by filtration and slurried in 30 ml of a solution of methanol/concentrated ammonium hydroxide (v:v, 1:1). The resin was collected by filtration and the filtrate concentrated in vacuo at 50° C. to give 0.14 g of 1-(2-desoxy-2,2-difluoro-β-D-xylofuranosyl)cytosine.

NMR (CD$_3$OD, 90 mHz, δ) 3.72–4.34 (m, 4H), 4.78 (s, 4H), 5.86 (d, J=8 Hz, 1H), 6.17 (d, J=15 Hz, 1H), 7.78 (d, J=8 Hz, 1H). Mass spec. m/e=263=P The compound labeled B was chromatographed on a Whatman 50 cm ODS-3 reverse phase prep column using water/methanol (v:v, 1:1) as the eluent to afford 0.06 g of 1-(2-desoxy-2,2-difluoro-α-D-xylofuranosyl)cytosine.

NMR (CD$_3$OD, 90 mHz, δ) 3.53–3.9 (m, 2H), 4.1–4.57 (m, 2H) 4.83 (s, 4H), 5.9 (d, J=8 Hz, 1H), 6.3 (dd, J=7 Hz, 12 Hz, 1H) 7.55 (d, J=8 Hz, 1H). Mass spec. m/e=263=P

EXAMPLE 6

1-(6-Amino-9H-purin-9-yl)-2-desoxy-2,2-difluororibose

A. 1-(6-Chloro-9H-purin-9-yl)-3,5-bis(t-butyldimethylsiloxy)- 2-desoxy-2,2-difluororibose To a solution of 0.77 g (5.0 mmol) of 6-chloro-purine in 50 ml of tetrahydrofuran was added 1.31 g (5.0 mmol) of triphenylphosphine and 0.87 g (5.0 mmol) of diethyl azodicarboxylate. To this solution was added a solution of 1.99 g (5.0 mmol) of 3,5-bis(t-butyldimethylsiloxy)- 1-hydroxy-2-desoxy-2,2-difluororibose in tetrahydrofuran. The reaction mixture was stirred at room temperature for approximately 60 hours and an additional 0.66 g (1.7 mmol) of 3,5-bis(t-butyldimethylsiloxy)-1-hydroxy-2-desoxy-2,2-difluororibose was added to the reaction mixture. The mixture was stirred for an additional 6 hours at room temperature. The solvent was evaporated under vacuum and the residue was stirred in a small amount of diethyl ether overnight. The precipitated solid was removed by vacuum filtration and the filtrate was concentrated under vacuum to dryness. The residue was chromatographed over 70 g of silica and eluted with chloroform. Fractions containing the major component were combined and the solvent was evaporated therefrom to provide 1.0 g of 1-(6-chloro-9H-purin-9-yl)-3,5-bis(t-butyldimethylsiloxy)-2-desoxy-2,2-difluororibose. The structure of the product was verified by NMR. Mass spec.=477 [534-(t-butyl)]

B. 1-(6-Amino-9H-purin-9-yl)-3,5-bis(t-butyldimethylsiloxy)- 2-desoxy-2,2-difluororibose A solution of 0.5 g (0,936 mmol) of 1-(6-chloro-9H-purin-9-yl)-3,5-bis(t-butyldimethylsiloxy)-2-desoxy-2,2-difluororibose dissolved in 75 ml of absolute ethanol was saturated with anhydrous ammonia at about 0° C. The reaction flask was sealed, and the mixture was allowed to warm to room temperature. The mixture was stirred for about 72 hours at room temperature and the volatiles were evaporated under reduced pressure to provide 420 mg of 1-(6-amino-9H-purin-9-yl)-3,5-bis(t-butyldimethylsiloxy)-2-desoxy-2,2-difluororibose. Mass spec=458 [515-(t-butyl)]

C. A solution of 100 mg (0.194 mmol) of 1-(6-amino-9H-purin-9-yl)-3,5-bis(t-butyldimethylsiloxy)-2-desoxy-2,2-difluororibose dissolved in 25 ml of methylene chloride cooled to about 0° C. with an external ice bath was saturated with anhydrous hydrogen bromide gas. The mixture was stirred at about 0° C. for about 4 hours, and nitrogen was bubbled through the reaction mixture. The mixture was filtered and the collected solid was washed with methanol to provide 110 mg of solid. The solid was purified by HPLC to provide 12.1 mg of β-1-(6-amino-9H-purin-9-yl)-2-desoxy-2,2-difluororibose and 6.3 mg of α-1-(6-amino-9H-purin-9-yl)-2-desoxy-2,2-difluororibose.

NMR for β-isomer. NMR (CD$_3$OD, 30 mHz, δ), 3.8–4.65 (m, 4H); 4.83 (bs, 4H); 6.33 (dd, 1H); 8.22 (s, 1H); 8.4 (s, 1H). mass spec. m/e=287

EXAMPLE 7

A. 1-(2,6-Dichloro-9H-purin-9-yl)-3,5-bis(t-butyldimethylsiloxy)- 2-desoxy-2,2-difluororibose To a solution of 1.89 g (10.0 mmol) of 2,6-dichloropurine in 100 ml of tetrahydrofuran was added 2.62 g (10.0 mmol) of triphenylphosphine and 1.74 g (10.0 mmol) of diethyl azodicarboxylate. To this mixture was added a solution of 3.98 g (10.0 mmol) of 3,5-bis(t-butyldimethylsiloxy)-1-hydroxy-2-desoxy-2,2-difluororibose in 25 ml of tetrahydrofuran and the mixture was stirred at room temperature overnight. The precipitated solid was removed by vacuum filtration and the filtrate was concentrated under vacuum. The residue was dissolved in 100 ml of diethyl ether and the solution was stirred at room temperature overnight. The mixture was filtered and the filtrate was evaporated to dryness under vacuum. The residue was dissolved in 25 ml of ethyl acetate, and the mixture was set in the refrigerator. The mixture was filtered and the filtrate was chromatographed by HPLC while eluting with hexane/ethyl acetate (4/1, v/v). The first chromaphore containing fractions were combined and the solvent was evaporated therefrom to provide 2.5 g of 1-(2,6-dichloro-9H-purin-9-yl)-3,5-bis(t-butyldimethylsiloxy)-2-desoxy-2,2-difluororibose. m/e= [568-(t-butyl)]=511

B. 1-(2-Chloro-6-oxo-1H,9H-purin-9-yl)-2-desoxy-2,2-difluororibose and 1-(2-chloro-6-bromo-9H-purin- 9-yl)-2-desoxy-2,2-difluororibose.

A solution of 0.5 g (0.88 mmol) of 1-(2,6-dichloro-9H-purin-9-yl)-3,5-bis(t-butyldimethylsiloxy)-2-desoxy-2,2-difluororibose dissolved in 100 ml of methylene chloride cooled to about 0° C. was saturated with anhydrous hydrogen bromide gas. The mixture was stirred at 0° C. for about 7 hours and then at room temperature for about 16 hours. The mixture was filtered, and the precipitated solid was dissolved in methanol. The methanolic solution was concentration under vacuum to provide 160 mg of a mixture of 1-(2-chloro-6-oxo-1H,9H-purin-9-yl)-2-desoxy-2,2-difluororibose and 1-(2-chloro-6-bromo-9H-purin-9-yl)-2-desoxy-2,2-difluororibose as a light yellow solid. m/e=322 and 386 respectively.

C. 1-(2-Chloro-6-oxo-1H,9H-purin-9-yl)-2-desoxy-2,2-difluororibose

A mixture of 1.18 g (3 mmol) of 1-(2-chloro-6-oxo-1H, 9H-purin-9-yl)-2-desoxy-2,2-difluororibose and 1-(2-chloro-6-bromo-9H-purin-9-yl)-2-desoxy-2,2-difluororibose dissolved in 11 ml of 1.0N sodium hydroxide was stirred at room temperature for three hours. The pH of the mixture was lowered to about 7 with 2N hydrochloric acid. The mixture was concentrated under vacuum at about 45° C. The residue was slurried in warm methanol, filtered and this procedure was repeated. The filtrates were combined and the solution was concentrated under vacuum at 15° C. to provide 1.36 g of 1-(2-chloro-6-oxo-1H,9H-purin-9-yl)-2-desoxy-2,2-difluororibose. m/e=322.

D. This is the preferred synthesis of 1-(2-amino-6-oxo-1H,9H-purin-9-yl)-2-desoxy-2,2-difluororibose. However, the material prepared by the following reaction was not biologically evaluated, but rather was used as a reference standard for the subsequent synthesis of the compound which was biologically evaluated.

To a suspension of 1.3 g of 1-(2-chloro-6-oxo-1H,9H-purin-9-yl)-2-desoxy-2,2-difluororibose in 30 ml of absolute ethanol at a temperature of about 0° C. was added anhydrous ammonia. The mixture was placed in a closed reaction vessel and heated at about 150° C. overnight. The mixture was cooled and the solid was collected. The filtrate was suspended in 15 ml of hot methanol and the mixture was again filtered. The filtrate was concentrated under vacuum and the residue was chromatographed by HPLC using water methanol (9/1, v/v) as the eluent at a flow rate of 4 ml/minute to provide 10 mg of α-1-(2-amino-6-oxo-1H,9H-purin-9-yl)-2-desoxy-2,2-difluororibose and 5 mg of β-1-(2-amino-6-oxo-1H,9H-purin-9-yl)-2-desoxy-2,2-difluororibose. m/e=303

The compounds which were biologically tested were prepared as follows:

To 0.26 g of a mixture of 1-(2-chloro-6-oxo-1H,9H-purin-9-yl)-2-desoxy-2,2-difluororibose and 1-(2-chloro-6-bromo-9H-purin-9-yl)-2-desoxy-2,2-difluororibose in 10 ml of absolute ethanol at about 0° C. was added anhydrous ammonia for 20 minutes. The flask was sealed and placed in an oil bath at about 150° C. for about 16 hours. The volatiles were evaporated under reduced pressure and the residue was purified by standard procedures to provide 9.6 mg of α-1-(2-chloro-6-amino-9H-purin-9-yl)-2-desoxy-2,2-difluororibose having m/e=322; 8.2 mg of β-1-(2-chloro-6-amino-9H-purin-9-yl)-2-desoxy-2,2-difluororibose having m/e=322 and an NMR (CD$_3$OD, 300 mHz, δ) 3.8–4.65 (m, 4H); 4.93 (bs, 4H); 6.25 (dd, 1H); 8.35 (s, 1H); 6.5 mg of a mixture of α- and β-1-(2,6-diamino-9H-purin-9-yl)-2-desoxy-2,2-difluororibose having (m+1)e=304 and m/e calc. 303.1017; obs. 303.1009; 9.0 mg of 1-(2-amino-6-oxo-1H,9H-purin-9-yl)-2-desoxy-2,2-difluororibose having (m+H)/e and calc. 304.0857; obs. 304.0857; and NMR (CD$_3$OD, 300 mHz, δ) 3.85–4.65 (m, 4H); 4.9 (bs, 5H); 6.15 (dd, 1H); 7.98 (s, 1H); and 9.0 mg of α- and β-1-(2,6-dioxo-1H,3H,9H-purin-9-yl)-2-desoxy-2,2-difluororibose having m/e=304.

The present invention provides a method of treating susceptible neoplasms in mammals comprising administering to a mammal in need of such treatment a pharmaceutically effective amount of a compound of formula I. The method comprises administering the compound to the mammal by various routes including the oral, rectal, transdermal, subcutaneous, intravenous, intramuscular or intranasal routes.

The term "pharmaceutically effective amount", as defined herein, refers to an appropriate amount of a compound of formula I which is capable of providing chemotherapy to mammals. The active compounds are effective over a wide dosage range. For example, dosages per day will normally fall within the range of about 0.1 to about 1200 mg/kg of body weight. In the treatment of adult humans, the range of about 0.1 to about 50 mg/kg, in single or divided doses, is preferred. However, it will be understood that the amount of compound actually administered will be determined by a physician, in the light of the relevant circumstances including the condition to be treated, the particular compound to be administered, the chosen route of administration, the age, weight, and response of the individual patient, and the severity of the patient's symptoms, and therefore the above dosage ranges are not intended to limit the scope of the invention in any way.

The term "susceptible neoplasm", as defined herein, represents an abnormal growth of tissue in mammals capable of being treated by a compound of formula I. While the compounds of formula I are effective against tumors, both solid and non-solid type, the compounds are effective in controlling the growth of rapidly dividing cells because of the compounds' cytotoxic nature. It is a special feature of these compounds that they have a broad spectrum of activity, and are accordingly useful against a variety of tumors.

The compounds of the present method are preferably administered as a pharmaceutical formulation. Therefore, as yet another embodiment of the present invention, a pharmaceutical formulation useful for treating susceptible neoplasms in mammals is provided comprising a compound of formula I with a pharmaceutical carrier, diluent or excipient therefor.

The active ingredient will be present in the formulation in the range of about 1% to about 90% by weight. The active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples represent specific pharmaceutical formulations employing compounds comprehended by the present method. The formulations may employ as active compounds any of the compounds of Formula I. The examples are illustrative only and are not intended to limit the scope of the invention in any way.

Formulation 1

Hard gelatin capsules are prepared using the following ingredients:

|  | Quantity (mg/capsule) |
|---|---|
| 1-(4-amino-5-methyl-2-oxo-1H-pyrimidin-1-yl)-2-desoxy-2,2-difluororibose | 250 |
| Starch dried | 200 |
| Magnesium stearate | 10 |

The above ingredients are mixed and filled into hard gelatin capsules in 460 mg quantities.

Formulation 2

A tablet formula is prepared using the ingredients below:

|  | Quantity (mg/tablet) |
|---|---|
| 1-(2-oxo-4-amino-1H-pyrimidin-1-yl)-2-desoxy-2,2-difluororibose | 250 |
| Cellulose, microcrystalline | 400 |
| Silicon dioxide, fumed | 10 |
| Stearic acid | 5 |

The components are blended and compressed to form tablets each weighing 665 mg.

Formulation 3

An aerosol solution is prepared containing the following components:

|  | Weight % |
|---|---|
| 1-(2,4-dioxo-1H,3H-pyrimidin-1-yl)-2-desoxy-2,2-difluororibose | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then placed in a stainless steel container and diluted with the remainder of the propellant. The valve units are then fitted to the container.

Formulation 4

Tablets each containing 60 mg of active ingredient are made up as follows:

| | |
|---|---|
| 1-(4-amino-2-oxo-1H-pyrimidin-1-yl)-2-desoxy-2,2-difluororibose | 60 mg |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |

The difluoronucleoside starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| 1-(4-amino-2-oxo-1H-pyrimidin-1-yl)-2-desoxy-2,2-difluoroxylose | 80 mg |
| Starch | 59 mg |
| Microcrystalline cellulose | 59 mg |
| Magnesium stearate | 2 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of nucleoside are made as follows:

| | |
|---|---|
| 1-(2,4-dioxo-1H,3H-pyrimidin-1-yl)-2-desoxy-2,2-difluororibose | 225 mg |
| Saturated fatty acid glycerides to | 2 g |

The nucleoside is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| 1-(4-amino-5-methyl-2-oxo-1H-pyrimidin-1-yl)-2-desoxy-2,2-difluororibose | 50 mg |
| Sodium carboxymethyl cellulose | 50 mg |
| Syrup | 1.25 ml |
| Benzoic acid solution | 0.10 ml |
| Flavor | q.v. |

-continued

| Color | q.v. |
|---|---|
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation is prepared as follows:

| 1-(4-amino-2-oxo-1H-pyrimidin-1-yl)-2-desoxy-2,2-difluoro ribose | 100 mg |
|---|---|
| isotonic saline | 1000 ml |

The solution of the above ingredients is administered intravenously at a rate of 1 ml/minute to a mammal in need of treatment from susceptible neoplasms.

The activity of representative compounds employed in the present invention has been demonstrated in standard screens commonly used by those in the art in testing compounds for potential antitumor drugs. For example, these screens have been used to demonstrate the antitumor activity of commercially available cancer drugs such as the vinca alkaloids. See, e.g., Miller et al., in *J. Med. Chem.* Vol. 20, No. 3 409 (1977) and Sweeney, et al., in *Cancer Research* 38, 2886 (1978).

The compounds represented by formula I employed in the present invention are cytostatic in that they inhibit the growth of human leukemic cells (CCRF-CEM cell line). Table 1 below gives the results of such testing of several compounds representative of those in Formula I. In the Table, column 1 gives the name of the compound and column 2 the $IC_{50}$ (concentration giving 50% growth inhibition) in mcg/ml.

TABLE 1

| Cytotoxicity Screen | |
|---|---|
| Compound Name | $IC_{50}$ mcg/ml |
| 1-(4-amino-2-oxo-1H-pyrimidin-1-yl)-2-desoxy-2,2-difluororibose | 0.0039 |
| | 0.0057 |
| | 0.0068 |
| | 0.0260 |
| 1-(4-amino-2-oxo-1H-pyrimidin-1-yl)-2-desoxy-2,2-difluoroxylose | 0.3 |
| 1-(2,4-dioxo-1H,3H-pyrimidin-1-yl)-2-desoxy-2,2-difluororibose | 5.4 |
| 1-(4-amino-5-methyl-2-oxo-1H-pyrimidin-1-yl)-2-desoxy-2,2-difluororibose | 0.3 |
| β-1-(6-amino-9H-purin-9-yl)-2-desoxy-2,2-difluororibose | 0.5 |
| α-1-(6-amino-9H-purin-9-yl)-2-desoxy-2,2-difluororibose | 6.9 |
| α-1-(2-chloro-6-amino-9H-purin-9-yl)-2-desoxy-2,2-difluororibose | >20.0 |
| β-1-(2-chloro-6-amino-9H-purin-9-yl)-2-desoxy-2,2-difluororibose | 0.4 |
| 1-(2,6-diamino-9H-purin-9-yl)-2-desoxy-2,2-difluororibose | 0.075 |
| 1-(2-amino-6-oxo-1H,9H-purin-9-yl)-2-desoxy-2,2-difluororibose | 0.10 |
| 1-(2,6-dioxo-1H,3H,9H-purin-9-yl)-2-desoxy-2,2-difluororibose | 0.30 |

To further demonstrate the ability of the compounds of formula I to treat susceptible neoplasms in mammals, the compounds of Example 1, 1-(4-amino-2-oxo-1H-pyrimidin-1-yl)-2-desoxy-2,2-difluororibose, Example 5, 1-(4-amino-2-oxo-1H-pyrimidin-1-yl)-2-desoxy-2,2-difluoroxylose, and Example 6, 1-(6-amino-9H-purin-9-yl)-2-desoxy-2,2-difluororibose, were tested in animals bearing a tumor system representative of L1210V lymphocytic leukemia.

The study testing the efficacy of these compounds against L1210V leukemia was initiated by an IP inoculation of $1\times10^6$ cells. Treatment was begun 24 hours after inoculation. The response to therapy was determined by comparing the mean life span of the ten treated animals to that of the ten control animals; prolongation of life in the treated animals beyond that of controls is expressed as a percentage. Table 2 gives the results of several experiments in mice bearing this tumor. In the Table, column 1 gives the example number of the compound tested; column 2, the experiment number; column 3, the dose level of the compound in mg/kg; column 4, the route of administration; column 5, the dosage schedule, that is, the days on which the compound was administered to the mice; column 6, the average increase in life span of the treated mice as compared to the control mice; column 7, the toxic deaths over the number of mice in each group; and column 8, the indefinite survivors, that is, the number of 45 day survivors in each group.

TABLE 2

| L1210V Lymphocytic Leukemia Tumor System | | | | | | | |
|---|---|---|---|---|---|---|---|
| Example No. of Compound Tested | Experiment No. | Dose Level mg/kg | Route of Administration | Dosage Schedule | Percent Increase Life Span | Toxic Deaths | Indefinite Survivors |
| 1 | 1 | 20.0 | IP | Days | 60 | 0/10 | 0 |
| | | 10.0 | | 1,5,9 | 66 | 1/10 | 0 |
| | | 5.0 | | | 66 | 0/10 | 0 |
| | | 2.5 | | | 60 | 0/10 | 0 |
| | | 1.25 | | | 50 | 0/10 | 0 |
| | 2 | 2.0 | IP | Daily | 0 | 0/10 | 0 |

TABLE 2-continued

| | | L1210V Lymphocytic Leukemia Tumor System | | | | | |
|---|---|---|---|---|---|---|---|
| Example No. of Compound Tested | Experiment No. | Dose Level mg/kg | Route of Administration | Dosage Schedule | Percent Increase Life Span | Toxic Deaths | Indefinite Survivors |
| | | 1.0 | | for 10 | 0 | 0/10 | 0 |
| | | 0.5 | | Days | 13 | 0/10 | 0 |
| | 3 | 200.0 | IP | Day 1 | 34 | 0/10 | 0 |
| | | 100.0 | | only | 26 | 0/10 | 0 |
| | | 50.0 | | | 30 | 0/10 | 0 |
| | | 25.0 | | | 23 | 0/10 | 0 |
| | 4 | 4.0 | PO | Daily | 2 | 4/10 | 0 |
| | | 2.0 | | for 10 | 18 | 1/10 | 0 |
| | | 1.0 | | days | 15 | 0/10 | 0 |
| | | 0.5 | | | 8 | 0/10 | 0 |
| | 5 | 4.0 | IP | Daily | 44 | 0/10 | 0 |
| | | 2.0 | | for 9 | 136 | 0/10 | 0 |
| | | 1.0 | | days | 104 | 0/10 | 0 |
| | | 0.5 | | | 74 | 0/10 | 0 |
| 5 | 1 | 30.0 | IP | Daily for 10 days | 57 | 0/10 | 0 |
| 6 | 1 | 200.0 | IP | Daily | 18 | 0/7 | 0 |
| | | 100.0 | | for 9 days | 16 | 0/7 | 0 |

The compounds of Example 1, 1-(4-amino-2-oxo-1H-pyrimidin-1-yl)-2-desoxy-2,2-difluororibose, and Example 5, 1-(4-amino-2-oxo-1H-pyrimidin-1-yl)-2-desoxy-2,2-difluoroxylose, also demonstrated activity in additional tumor test systems. These systems include the 6C3HED lymphosarcoma, also known as the Gardner lymphosarcoma (6C3HED); the CA-755 adenocarcinoma (CA755); the P1534J lymphatic leukemia (P1534J); and the X5563 plasma cell myeloma (X5563). Each of these systems is described in detail below.

6C3HED—The 6C3HED lymphosarcoma was obtained in 1979 from the Division of Cancer Treatment, N.C.I., tumor bank maintained at E.G. and G. Mason Research (Worchester, Mass.). First passage tumor was stored in liquid nitrogen using standard techniques. The transplanted tumor was re-established from the tumor bank every six months or as needed. The tumor is maintained by serial passage twice weekly in C3H mice (Charles River; Wilmington, Mass.).

CA755—The adenocarcinoma 755 is an undifferentiated mammary carcinoma which was obtained in 1980 from the Division of Cancer Treatment, N.C.I., tumor bank maintained at E.G. and G. Mason Research (Worchester, Mass.). First passage tumor was stored in liquid nitrogen using standard techniques. The transplanted tumor was re-established from the tumor bank every six months or as needed. The tumor is maintained by serial passage once a week in C57BL/6 female mice (Jackson Laboratory; Bar Harbor, Me.).

P1534J—The P1534J lymphocytic leukemia (solid form) was obtained in 1973 from the Jackson Laboratory (Bar Harbor, Me.). First passage tumor was stored in liquid nitrogen using standard techniques. Subsequent replenishment of the tumor bank with this tumor was accomplished from first passage tumor. The transplanted tumor was re-established from the tumor bank every six months or as needed. The tumor is maintained by serial passage once a week in DBA/2 mice (Charles River; Wilmington, Mass.).

X5563 Myeloma—the tumor is maintained in C3H mice.

The following procedure was employed in demonstrating the activity of these compounds against the tumor systems. The tumor was removed from passage animals and minced into 1 to 3 mm square fragments using sterile techniques. Tumor pieces were checked for sterility using both Antibiotic Medium 1 and Brain Heart Infusion (Difco; Detroit, Mich.). Recipient mice were shaved and tumor pieces were implanted subcutaneously in the axillary region by trocar. Drug therapy on the appropriate schedule was initiated on the day after tumor implant. The compound was dissolved in saline for all experiments. All animals were weighed at the beginning and end of drug treatment. Food and water were provided ad libitum. On days 10 to 20, two dimensional measurements (width and length) of all tumors were taken using vernier calipers. Tumor weights were calculated from these measurements using the following formula:

$$\text{Tumor Weight (mg)} = \text{Tumor Length (mm)} \times \text{Tumor Width (mm)}^2/2$$

For all data, the tumor weight was rounded to the nearest tenth of a gram for analysis. No group is included in the analysis for therapeutic activity in which deaths attributable to drug toxicity exceeded 30 percent of the treated group.

In Table 3 which follows, column 1 gives the example number of the compound tested; column 2 provides the tumor system; column 3, the dose level; column 4, the route administered; column 5, the dosage schedule; column 6, the percent inhibition of the tumor; and column 7, the toxic deaths observed prior to completion of the study.

TABLE 3

Activity of Example 1 Against A Variety of Tumor Models

| Example No. of Compound Tested | Tumor System | Dose Level mg/kg | Route of Administration | Dosage Schedule | Percent Inhibition of Tumor | Toxic Deaths |
|---|---|---|---|---|---|---|
| 1 | 6C3HED | 20.0 | IP | Days 1,5,9 | 95 | 0/7 |
|   |        | 10.0 |    |            | 88 | 0/7 |
|   |        | 5.0  |    |            | 49 | 0/7 |
|   |        | 2.5  |    |            | 1  | 0/7 |
|   |        | 1.25 |    |            | 0  | 0/7 |
|   | 6C3HED | 0.4  | IP | Daily for 8 Days | 8 | 0/10 |
|   |        | 0.2  |    |            | 0  | 0/10 |
|   |        | 0.1  |    |            | 0  | 0/10 |
|   |        | 0.05 |    |            | 0  | 0/10 |
|   | CA755  | 20.0 | IP | Days 1,5,9 | 94 | 0/10 |
|   |        | 10.0 |    |            | 86 | 0/10 |
|   |        | 5.0  |    |            | 85 | 0/10 |
|   |        | 2.5  |    |            | 44 | 0/10 |
|   |        | 1.25 |    |            | 0  | 0/10 |
|   | P1534J | 20.0 | IP | Days 1,5,9 | 92 | 1/10 |
|   |        | 10.0 |    |            | 71 | 2/10 |
|   |        | 5.0  |    |            | 47 | 0/10 |
|   |        | 2.5  |    |            | 30 | 0/10 |
|   |        | 1.25 |    |            | 8  | 0/10 |
|   | X5563  | 20.0 | IP | Days 1,5,9 | 100 | 0/10 |
|   |        | 10.0 |    |            | 98 | 0/10 |
|   |        | 5.0  |    |            | 89 | 0/10 |
|   |        | 2.5  |    |            | 52 | 1/10 |
|   |        | 1.25 |    |            | 11 | 1/10 |
| 5 | X5563  | 30.0 | IP | Daily for 9 days | 28 | 0/10 |

The compounds employed in the present method are also effective for the treatment of viral infections, and more particularly in the treatment of infections caused by viruses of the herpes genus. The compounds are effectively administered orally, topically or parenterally. In general, dosage rates in the range of from about 5 mg/kg to about 500 mg/kg are useful. It is more preferred to administer at rates in the range of from about 10 mg/kg to about 100 mg/kg.

We claim:

1. A method of treating susceptible neoplasms in mammals comprising administering to a mammal in need of such treatment a therapeutically effective amount of a compound of the formula

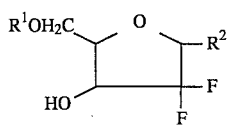

wherein:

$R^1$ is hydrogen;

$R^2$ is a base defined by one of the formulae

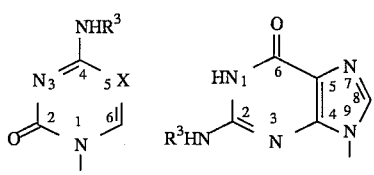

X is C–$R^4$;

$R^3$ is hydrogen;

$R^4$ is hydrogen, $C_1$–$C_4$ alkyl, bromo, fluoro, chloro or iodo;

and the pharmaceutically-acceptable salts thereof.

2. The method of claim 1 in which the compound is 1-(4-amino-2-oxo-1H-pyrimidin-1-yl)-2-desoxy-2,2-difluororibose or a pharmaceutically acceptable salt thereof.

3. The method of claim 1 in which the compound is 1-(4-amino-2-oxo-1H-pyrimidin-1-yl)-2-desoxy-2,2-difluoroxylose or a pharmaceutically acceptable salt thereof.

4. The method of claim 1 in which the compound is 1-(2,4-dioxo-1H,3H-pyrimidin-1-yl)-2-desoxy-2,2-difluororibose or a pharmaceutically acceptable salt thereof.

5. The method of claim 1 in which the compound is 1-(4-amino-5-methyl-2-oxo-1H-pyrimidin-1-yl)-2-desoxy-2,2-difluororibose or a pharmaceutically acceptable salt thereof.

6. The method of claim 1 wherein the susceptible neoplasm is selected from the group consisting of leukemias, sarcomas, carcinomas, and myelomas.

7. The method of claim 6 employing 1-(4-amino-2-oxo-1H-pyrimidin-1-yl)-2-desoxy-2,2-difluororibose or a pharmaceutically acceptable salt thereof.

* * * * *